US009801797B2

(12) United States Patent
Koehle et al.

(10) Patent No.: US 9,801,797 B2
(45) Date of Patent: Oct. 31, 2017

(54) FORMULATION COMPRISING ESTER QUATS BASED ON ISOPROPANOLAMINE

(71) Applicant: Evonik Industries AG, Essen (DE)

(72) Inventors: Hans-Juergen Koehle, Mainhausen (DE); Kurt Seidel, Jossgrund (DE); Peter Schwab, Essen (DE); Ursula Westerholt, Essen (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 14/222,104

(22) Filed: Mar. 21, 2014

(65) Prior Publication Data

US 2014/0286889 A1 Sep. 25, 2014

(30) Foreign Application Priority Data

Mar. 22, 2013 (DE) ........................ 10 2013 205 092

(51) Int. Cl.
| | | |
|---|---|---|
| *A61K 8/41* | (2006.01) | |
| *A61K 8/34* | (2006.01) | |
| *A61Q 5/12* | (2006.01) | |
| *A61Q 5/02* | (2006.01) | |
| *A61Q 19/10* | (2006.01) | |
| *A61Q 5/06* | (2006.01) | |
| *A61Q 5/00* | (2006.01) | |
| *A61Q 19/00* | (2006.01) | |

(52) U.S. Cl.
CPC .............. *A61K 8/416* (2013.01); *A61K 8/342* (2013.01); *A61Q 5/12* (2013.01); *A61Q 5/002* (2013.01); *A61Q 5/02* (2013.01); *A61Q 5/06* (2013.01); *A61Q 19/00* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 5,718,891 A | 2/1998 | Prat et al. | |
| 6,242,499 B1 | 6/2001 | Gruning et al. | |
| 6,376,455 B1 * | 4/2002 | Friedli et al. ................. | 510/515 |
| 6,485,733 B1 * | 11/2002 | Huard ...................... | A61K 8/02 |
| | | | 424/400 |
| 7,074,419 B2 | 7/2006 | Dietz et al. | |
| 8,211,972 B2 | 7/2012 | Meyer et al. | |
| 8,466,248 B2 | 6/2013 | Meyer et al. | |

(Continued)

FOREIGN PATENT DOCUMENTS

| | | |
|---|---|---|
| DE | 24 30 140 C3 | 2/1976 |
| DE | 3608093 A1 | 9/1987 |

(Continued)

OTHER PUBLICATIONS

Tego® Alkanol 18, https://www.ulprospector.com/en/na/PersonalCare/Detail/1483/52298/TEGO-Alkanol-18, accessed Dec. 22, 2015.*

(Continued)

*Primary Examiner* — Bethany Barham
*Assistant Examiner* — Barbara Frazier
(74) *Attorney, Agent, or Firm* — Scully Scott Murphy and Presser

(57) ABSTRACT

Cosmetic formulations including specific ester quats based on isopropanolamine are provided, as well as the use of these ester quats in cosmetics.

13 Claims, 4 Drawing Sheets

(56) References Cited

U.S. PATENT DOCUMENTS

| | | |
|---|---|---|
| 2004/0258651 A1 | 12/2004 | Pascaly et al. |
| 2007/0231289 A1* | 10/2007 | Gruning et al. .......... 424/70.28 |
| 2010/0192814 A1 | 8/2010 | Herzog et al. |
| 2013/0071343 A1 | 3/2013 | Herrwerth et al. |
| 2013/0078208 A1 | 3/2013 | Herrwerth et al. |
| 2013/0171087 A1 | 7/2013 | Herrwerth et al. |
| 2013/0204021 A1 | 8/2013 | Hartung et al. |

FOREIGN PATENT DOCUMENTS

| | | |
|---|---|---|
| DE | 3877422 T2 | 5/1993 |
| DE | 4308794 C1 | 4/1994 |
| DE | 10327871 A1 | 1/2005 |
| DE | 102008001788 A1 | 11/2009 |
| DE | 10 2010 029 606 A1 | 12/2011 |
| EP | 0 293 953 A2 | 12/1988 |
| EP | 0293955 | 12/1988 |
| EP | 0483195 | 5/1992 |
| EP | 0835862 B1 | 4/1998 |
| EP | 1125574 B1 | 8/2001 |
| EP | 2168564 A2 | 3/2010 |
| WO | WO9101295 | 2/1991 |
| WO | WO 99/35223 A1 | 7/1999 |
| WO | WO2004112731 A2 | 12/2004 |
| WO | WO2006034992 | 4/2006 |
| WO | WO2008092676 A1 | 8/2008 |
| WO | WO2009138306 A1 | 11/2009 |

OTHER PUBLICATIONS

Evonik Industries, "Tego® Amid S 18" (Apr. 2008).*
Evonik Industries, "TEGO(R) Alkanol 16, TEGO(R) Alkanol 18, TEGO(R) Alkanol 1618" (Apr. 2008).*
Shapiro, I., et al., "Environmentally Friendly Ester Quats", Cosmetics and Toiletries Magazine, Dec. 1994, vol. 109, pp. 77-80.
Brock, M., et al., "Neue Entwicklungen auf dem Gebiet der Waescheweichspueler", Tens. Surf. Det., 30, pp. 394-399, 1993, English language abstract only.
Lagerman, R., et al. "Synthesis and Performance of Ester Quaternary Biodegradable Softners", JAOCS, Jan. 1994, pp. 97-100, vol. 71, No. 1.
Puchta, R., et al., "A New Generation of Softners", Tenside Surf. Det. 30, May 1993, 3, pp. 186-191.
European Search Report dated Feb. 16, 2015 received in related Application No. 14157418.6-1458.
Schrader, K. et al., "Grundlagen und Rezepturen der Kosmetika" ["Principles and Formulations of Cosmetics"], 1989, 2nd edition, page 329 to 341, Hüthig Buch Verlag Heidelberg.

* cited by examiner

FORMULATION COMPRISING ESTER QUATS BASED ON ISOPROPANOLAMINE

FIELD OF THE INVENTION

The present invention relates to cosmetic formulations comprising specific ester quats based on isopropanolamine, and to the use of these ester quats in cosmetics.

PRIOR ART

DE3608093 describes quaternary ammonium compounds comprising two 2-acyloxyalkyl groups, the acyl groups of which are derived from saturated or unsaturated carboxylic acids having 12 to 22 carbon atoms, including dimethyldi (oleoyl-oxyisopropyl)ammonium methosulphate, and the use of such substances in textile-softening formulations.

DE3877422 describes similar quaternary ammonium compounds, the corresponding acyl groups of which contain at most 17 carbon atoms, including dimethyldi(palmitoyl-oxyisopropyl)ammonium chloride, and the use of such substances in textile-softening formulations, as well as their suitability for hair conditioners.

Ester quats obtainable hitherto, which are suitable for use in hair conditioning, are solid substances which are only converted to a formulatable form by using solvents, as a result of which it is stipulated which solvent will be present in the end formulation. This limits the degrees of freedom of the formulation options.

SUMMARY

The present invention provides a composition which exerts excellent conditioning effects on keratin fibers.

Notably, the present invention provides cosmetic formulations comprising 0.2 to 25% by weight, preferably 0.5 to 15% by weight, in particular 1 to 10% by weight, of at least one compound of general formula I)

$$(H_3C)_{\overline{a}}-N^+ \left( \begin{array}{c} R^1 \\ \diagup \\ O \\ R^2 \end{array} \right)_b \quad \text{general formula I)}$$

where $R^1$ is an acyl radical of an at least monounsaturated fatty acid with a chain length of 18 to 24 carbon atoms or the acyl radical of isostearic acid or ricinoleic acid,
where $R^2$ is an alkyl radical having 1 to 6 carbon atoms, preferably methyl, ethyl, propyl, isopropyl, particularly preferably methyl,
where $a=1$ to 3 and $b=1$ to 3, with the proviso that $a+b=4$,
40 to 99.8% by weight, preferably 50 to 99.5% by weight, in particular 60 to 99% by weight, of water, and, optionally, 0 to 8% by weight of a compound of general formula Ia)

$$(H_3C)_{\overline{c}}-N^+ \left( \begin{array}{c} R^{1a} \\ \diagup \\ O \\ R^{2b} \end{array} \right)_d \quad \text{general formula Ia)}$$

where $R^{1a}$ is an acyl radical of another carboxylic acid as defined for $R^1$ and
where $R^{2b}$ is an alkyl radical having 1 to 6 carbon atoms, preferably methyl, ethyl, propyl, isopropyl, particularly preferably methyl,
where $c=1$ to 3 and $d=1$ to 3,
with the proviso that $c+d=4$,
where the percentages by weight refer to the total formulation,
wherein
the compounds of general formula I) constitute at least 30% by weight, based on all of the compounds of general formula I) and Ia) present in the formulation.

The invention further provides the use of a compound of general formula I)

$$(H_3C)_{\overline{a}}-N^+ \left( \begin{array}{c} R^1 \\ \diagup \\ O \\ R^2 \end{array} \right)_b \quad \text{general formula I)}$$

where $R^1$ is an acyl radical of an at least monounsaturated fatty acid with a chain length of 18 to 24 carbon atoms or the acyl radical of isostearic acid or ricinoleic acid,
where $R^2$ is an alkyl radical having 1 to 6 carbon atoms, preferably methyl, ethyl, propyl, isopropyl, particularly preferably methyl,
where $a=1$ to 3 and $b=1$ to 3, with the proviso that $a+b=4$ for the cosmetic treatment of keratin fibers, in particular hair, with human hair being preferred.

The invention further provides a compound of general formula I)

$$(H_3C)_{\overline{a}}-N^+ \left( \begin{array}{c} R^1 \\ \diagup \\ O \\ R^2 \end{array} \right)_b \quad \text{general formula I)}$$

where $R^1$ is an acyl radical of isostearic acid,
where $R^2$ is an alkyl radical having 1 to 6 carbon atoms, preferably methyl, ethyl, propyl, isopropyl, particularly preferably methyl,
where $a=1$ to 3 and $b=1$ to 3
with the proviso that $a+b=4$.

A first advantage of the present invention is that the ester quats used are liquid at room temperature and can therefore easily be incorporated into a final consumer formulation without the use of solvents, as a result of which such a solvent does not necessarily have to be present in the formulation of the present invention.

A second advantage of the present invention is that the shine of the treated keratin fibers is increased.

A third advantage of the present invention is that the inventive compounds used develop a good effect even in small use amounts.

A fourth advantage of the present invention is that the inventive compounds used have little impact from an ecological point of view.

A fifth advantage of the present invention is that the inventive compounds used exhibit an improved conditioning effect on keratin fibers with longer rinse-off times than quaternary ester compounds known hitherto.

A sixth advantage of the present invention is that the inventive compounds have increased hydrolysis stability in the formulation.

A seven advantage of the present invention is that the inventive compounds do not crystallize out.

An eighth advantage of the present invention is that the inventive compounds are effective in relatively low use concentrations.

A ninth advantage of the present invention is that the inventive compounds protect hair colorants from being washed out.

A tenth advantage of the present invention is that the inventive compounds protect keratin fibers against thermally induced damage.

An eleventh advantage of the present invention is that the inventive compounds reduce the combing forces on wet and dry hair.

A twelfth advantage of the present invention is that the inventive compounds are particularly economical.

A thirteenth advantage of the present invention is that the inventive compounds and formulations can be prepared methanol-free.

DETAILED DESCRIPTION

Figure 1:
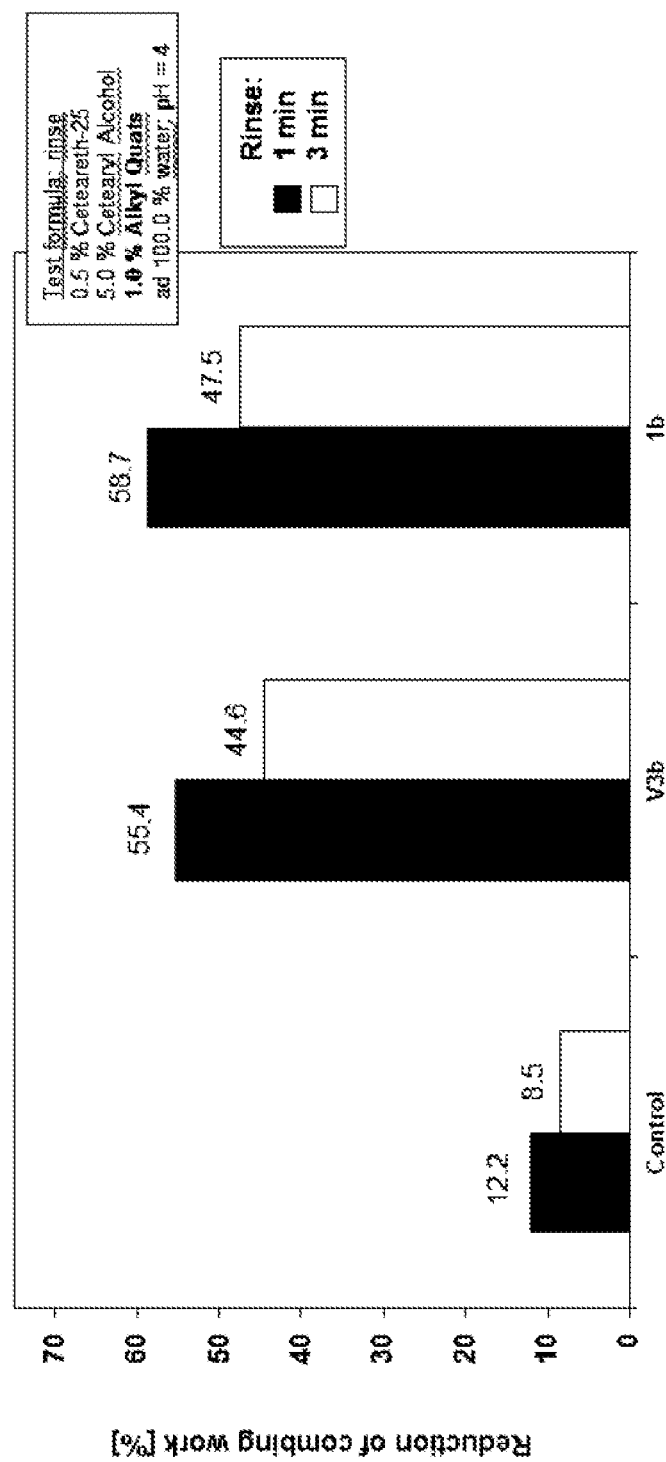
FIG. 1 illustrates the combing force measurements comparison of formulation 1b with V3b.

Unless stated otherwise, all of the percentages (%) stated are percentages by mass.

The quaternized fatty acid isopropanolamine ester salts used in the context of the invention can be prepared by relevant methods of preparative organic chemistry. Usually, the preparation of ester quats is based on a multistage process in which firstly the esterified alkanolamine is prepared by reacting an alkanolamine with carboxylic acids or corresponding derivatives, and the alkanolamine is then subsequently quaternized with a suitable reagent. In connection with the present invention, the alkanolamine used is dimethylmono-, methyldi- or triisopropanolamine or mixtures thereof, in particular methyldiisopropanolamine.

For suitable preparation processes, reference may be made to EP0483195, according to which trialkanolamine is partially esterified in the presence of hypophosphorous acid with fatty acids, air is passed through and then quaternization is carried out with dimethyl sulphate or ethylene oxide. The compounds listed therein serve as plasticizers for textiles. DE4308794 describes the preparation of solid ester quats by carrying out the quaternization of the triethanolamine esters in the presence of suitable dispersants. Overviews on this topic can be found for example under R. Puchta et al. in Tens. Surf. Det., 30, 186 (1993), M. Brock in Tens. Surf. Det., 30, 394 (1993), R. Lagerman et al. in J. Am. Chem. Soc., 71, 97 (1994) or under I. Shapiro in Cosm. Toil., 109, 77 (1994).

In formula I) of the present invention, and if b is >1, then the radicals $R^1$ can be identical or different.

When $R^1$ of formula I) is an acyl radical of an at least monounsaturated fatty acid with a chain length from 18 to 24 carbon atoms, it can contain one or more, for example two or three, double bonds.

Formulations preferred according to the invention are characterized in that $R^1$ as acyl radical of an at least monounsaturated fatty acid with a chain length of 18 to 24 carbon atoms is selected from the acyl radicals of the acids from the group comprising oleic acid, elaidic acid, vaccenic acid, gadoleic acid, icosenoic acid, cetoleic acid, erucic acid, nervonic acid, linoleic acid, alpha-linolenic acid, gamma-linolenic acid, calendula acid, punicic acid, alpha-elaeostearic acid, beta-elaeostearic acid, arachidonic acid, timnodonic acid, clupanodonic acid, and cervonic acid, oleic acid being particularly preferred.

According to the invention, it is also possible to use mixtures of these carboxylic acids.

Preferred formulations comprise at least one compound of the general formula I) where a=b=2.

A particularly preferred formulation according to the invention is characterized in that $R^1$ is the acyl radical of oleic acid and a=b=2.

In the formulation according to the invention, besides a compound of the general formula I), further compounds may be present which, apart from the radical $R^1$, correspond to the compound of the general formula I), i.e., the analogous radical $R^{1a}$ is the acyl radical of another carboxylic acid, in particular of another fatty acid.

In some embodiments, the formulations of the present invention can comprise a mixture of at least one compound of general formula I) and at least one compound of general formula Ia), as arises for example when using technical-grade fatty acid cuts which have longer or shorter acyl radicals than defined above for $R^1$.

The compounds of general formula I) constitute at least 30% by weight, preferably at least 50% by weight, particularly preferably at least 75% by weight, based on all of the compounds of general formula I) and Ia).

In some embodiments of the present invention, and if the mixture used is mixed plant oils with a carbon chain distribution, it is preferred that the following applies:

| Chain length of $R^1$ or $R^{1a}$ (' = number of double bond(s)) | Fraction based on total mixture |
|---|---|
| <C 16 | 0-2% by weight |
| C 16 | 4-7% by weight |
| C 16' | 0-2% by weight |
| C 18 | 0-4% by weight |
| C 18' | 55-65% by weight |
| C 18" | 15-25% by weight |
| C 18''' | 6-12% by weight |
| >C 18 | 0-4% by weight |

Preferred formulations of this embodiment comprise compounds of general formula I) or Ia) where a=b=c=d=2.

The invention further provides a compound of general formula I)

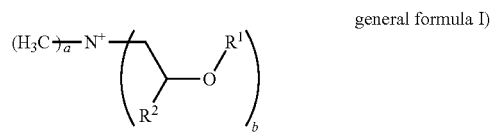

general formula I)

where R¹ is an acyl radical of isostearic acid,
where R² is an alkyl radical having 1 to 6 carbon atoms, preferably methyl, ethyl, propyl, isopropyl, particularly preferably methyl,
where a=1 to 3 and b=1 to 3
with the proviso that a+b=4.

Compounds of general formula I) preferred according to the invention are those where a=b=2, particularly preferably where R2=methyl.

Preferred formulations according to the invention comprise no fatty acids or fatty acid salts.

In some embodiments of the present invention, it has proven to be advantageous if the formulations according to the invention also comprise 0.5 to 20% by weight, preferably 1 to 10% by weight, in particular 2 to 7% by weight, of at least one fatty alcohol, where the percentages by weight refer to the total formulation.

The term "fatty alcohol" in this context is preferably understood as meaning an unbranched or branched mono-alcohol with an alkyl group of 8 to 30 carbon atoms, which may also be unsaturated. Preferred fatty alcohols are octanol, decanol, lauryl alcohol, isolauryl alcohol, anteisolauryl alcohol, myristyl alcohol, isomyristyl alcohol, cetyl alcohol, palmoleyl alcohol, stearyl alcohol, isostearyl alcohol, anteisostearyl alcohol, eicosanol, petroselinyl alcohol, Guerbet alcohol, arachyl alcohol, gadoleyl alcohol, behenyl alcohol, erucyl alcohol, hectacosanol, octacosanol, and melissyl alcohol, and mixtures thereof, in particular technical-grade mixtures, preferably technical-grade coconut or tallow fatty alcohols having 12 to 18, preferably having 16 to 18, carbon atoms, as well as the monounsaturated fatty alcohols, such as oleyl alcohol, elaidyl alcohol, delta-9-cis-hexadecenol, delta-9-octadecenol, trans-delta-9-octadecenol, cis-delta-11-octadecenol, trans-10,cis-12-hexadecadien-1-ol, octacosa-10,19-dien-1-ol and polyunsaturated fatty alcohols such as e.g. linoleyl alcohol (9Z, 12Z-octadecadien-1-ol), elaidolinoleyl alcohol (9E, 12E-octadecadien-1-ol), linolenyl alcohol (9Z, 12Z, 15Z-octadecatrien-1-ol), elaidolinolenyl alcohol (9E, 12E, 15-E-octadecatrien-1-ol), with mixtures of coconut or tallow fatty alcohols having 16 to 18 carbon atoms being particularly preferred.

In other embodiments of the present invention, it has proven to be advantageous if the formulations according to the invention also comprise 0.1 to 10% by weight, preferably 0.25 to 5% by weight, in particular 0.5 to 2.5% by weight, of at least one emulsifier, where the percentages by weight refer to the total formulation.

Emulsifiers preferred in this context are selected from the group of fatty alcohol alkoxylates, in particular the fatty alcohol ethoxylates. Particularly preferred fatty alcohol ethoxylates present are selected from the group comprising polyoxyethylene ethers of lauryl alcohol, CAS number 9002-92-0, macrogol lauryl ether, e.g., polyoxyethylene (4) lauryl ether (Laureth-4, INCI),
polyoxyethylene (9) lauryl ether Laureth-9 (INCI),
polyoxyethylene (23) lauryl ether Laureth-23 (INCI)
polyoxyethylene ethers of cetyl alcohol, CAS number 9004-95-9, e.g.,
polyoxyethylene (2) cetyl ether Ceteth-2 (INCI),
polyoxyethylene (10) cetyl ether Ceteth-10 (INCI)
polyoxyethylene (20) cetyl ether Ceteth-20 (INCI)
polyoxyethylene ethers of cetylstearyl alcohol, CAS number 68439-49-6, e.g.,
polyoxyethylene (6) cetylstearyl ether Ceteareth-6 (INCI)
polyoxyethylene (20) cetylstearyl ether Ceteareth-20 (INCI)
polyoxyethylene (25) cetylstearyl ether Ceteareth-25 (INCI)
polyoxyethylene ethers of stearyl alcohol, CAS number 9005-00-9, e.g.
polyoxyethylene (2) stearyl ether Steareth-2 (INCI)
polyoxyethylene (10) stearyl ether Steareth-10 (INCI)
polyoxyethylene (20) stearyl ether Steareth-20 (INCI)
polyoxyethylene ethers of oleyl alcohol, CAS number 9004-98-2, e.g.
polyoxyethylene (2) oleyl ether Oleth-2 (INCI)
polyoxyethylene (10) oleyl ether Oleth-10 (INCI)
polyoxyethylene (20) oleyl ether Oleth-20 (INCI)
or
polyoxyethylene (10) tridecyl ether (CAS number 24938-91-8) and Trideceth-10 (INCI).

Other emulsifiers that may be used can be selected from the group of polyol esters, in particular the glycerol esters and polyglycerol esters, in particular the polyglycerol esters. Preferably present (poly)glycerol esters are partial esters. Particularly preferred polyglycerol partial esters may include polyglycerol partial esters as described in EP-B-0 835 862, which are obtainable by esterification of a polyglycerol mixture with a degree of esterification of the polyglycerol between 30 and 75% and saturated or unsaturated, linear or branched fatty acids with 12 to 22 carbon atoms and dimer fatty acids with an average functionality of 2 to 2.4, esters of citric acid such as, for example, the O/W emulsifier glyceryl stearate citrate, (2-hydroxy-1,2,3-propanetricarboxylic acid-1,2,3-propanetriol monooctadecanoate, INCI Glyceryl Stearate Citrate, CAS 39175-72-9), the citric acid ester of glyceryl stearate, commercially available inter alia under the name AXOL C 62, glyceryl stearate citrate as described in WO2006034992 and WO2008092676 and glyceryl oleate citrate as described in WO2004112731, likewise simple polyglycerol esters, such as, for example, polygylcerol-3 distearate, polyglyceryl-10 stearate, polyglyceryl-6 distearate, mixed esters of polyglycerol and methyl glucose and stearic acid, such as, for example, polyglyceryl-3 methyl glucose distearate and (poly)glycerol partial esters with one or more carboxylic acids having 10 to 24 carbon atoms and radicals of a polyfunctional carboxylic acid.

In principle, sorbitan or sucrose esters can also be used as polyol esters. A customary combination is, for example, Sorbitan Stearate & Sucrose Cocoate.

Emulsifiers preferably present in a further embodiment of the present application are selected from the group of modified siloxanes, for example, those which also carry polyethers besides aliphatic groups based on alpha-olefins. Siloxane-based emulsifiers for oil-in-water emulsions must have a hydrophilic character, for which reason they are generally pure polyether siloxanes. Suitable examples include relatively hydrophobic polyether siloxanes as described in EP1125574, high molecular weight polyether siloxanes as described in EP2168564 and organomodified siloxane block copolymers as described in WO2009138306. Preferably present modified siloxanes can have a HLB value >8. Particularly preferred modified siloxanes include Bis-PEG/PPG-16/16 Dimethicone, PEG/PPG-16/16 Dimethicone, Bis-PEG/PPG-20/5 PEG/PPG-20/5 Dimethicone and Methoxy PEG/PPG-25/4 Dimethicone.

In connection with the present invention, the aforementioned emulsifiers produce particularly storage-stable formulations.

Formulations according to the invention comprising a compound of general formula I)

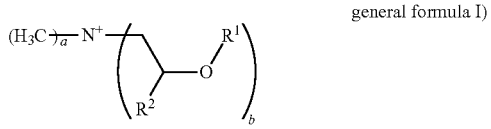

general formula I)

where $R^1$ is an acyl radical of isostearic acid,
where $R^2$ is an alkyl radical having 1 to 6 carbon atoms, preferably methyl, ethyl, propyl, isopropyl, particularly preferably methyl,
where a=1 to 3 and b=1 to 3, with the proviso that a+b=4, are preferably characterized in that they comprise, as emulsifier, those selected from the group of ethoxylated emulsifiers, such as, e.g., TEGINACID (Glyceryl Stearate, Ceteareth-20) or TEGINACID C (Ceteareth-25), or TEGO Acid S 40 P (PEG-40 Stearate) or TEGO Alkanol IC 20 (Isoceteth-20) or Laureth-23 or Steareth-20 or Steareth-21 or TEGO Care 165 (Glyceryl Stearate, PEG-100 Stearate) or TEGO Care 215 (Ceteareth-15, Glyceryl Stearate), organomodified siloxanes, such as, e.g., ABIL Care 85 (Bis-PEG/PPG-16/16 PEG/PPG-16/16 Dimethicone; Caprylic/Capric Triglyceride) or ABIL Care XL 80 (Bis-PEG/PPG-20/5 PEG/PPG-20/5 Dimethicone; Methoxy PEG/PPG-25/4 Dimethicone; Caprylic/Capric Triglyceride), cationic surfactants, such as, e.g., VARISOFT PATC (Palmamidopropyltrimonium Chloride) or VARISOFT TA 100 (Distearyldimonium Chloride) or VARISOFT BT 85 (Behentrimonium Chloride), sugar-based emulsifiers, such as, e.g., TEGO Care PS (Methyl Glucose Sesquistearate) or TEGO Care CG 90 (Cetearyl Glucoside), glycerol-based emulsifiers, such as, e.g., AXOL C62 Pellets (Glyceryl Stearate Citrate) or TEGO Care PL 4 (Polyglyceryl-4 Laurate), TEGO Care PSC 3 (Polyglyceryl-3 Stearate/Citrate), sugar- and glycerol-based emulsifiers, such as, e.g., TEGO Care 450 (Polyglyceryl-3 Methylglucose Distearate) or TEGO Care PS (Methyl Glucose Sesquistearate) and mixtures of the specified groups, such as, e.g., TEGO Care LTP (Sorbitan Laurate, Polyglyceryl-4 Laurate, Dilauryl Citrate).

In some embodiments of the present invention, the formulations according to the invention can comprise at least one further, additional component selected from the group of emollients,
coemulsifiers,
thickeners/viscosity regulators/stabilizers,
antioxidants,
hydrotropes (or polyols),
solids and fillers,
pearlescent additives,
deodorant and antiperspirant active ingredients,
insect repellents,
self-tanning agents,
preservatives,
conditioners,
perfumes,
dyes,
cosmetic active ingredients,
care additives,
superfatting agents, and/or
solvents.

Substances which can be used as exemplary representatives of the individual groups are known to the person skilled in the art and can be found for example in the German application DE 102008001788.4. This patent application is hereby incorporated by reference and thus forms part of the disclosure.

With respect to the further optional components and the amounts of these components used, reference is made expressly to the relevant handbooks known to the person skilled in the art, e.g., K. Schrader, "Grundlagen and Rezepturen der Kosmetika [Fundamentals and Formulations of Cosmetics]", $2^{nd}$ edition, page 329 to 341, Hüthig Buch Verlag Heidelberg.

The amounts of the respective additives are governed by the intended use.

Typical guide formulations for the respective applications are known prior art and are contained, for example, in the brochures of the manufacturers of the particular base materials and active ingredients. These existing formulations can generally be adopted without change. If necessary, however, the desired modifications can be undertaken without complication by means of simple experiments for the purposes of adaptation and optimization.

The formulation according to the invention can also comprise at least one compound of general formula II)

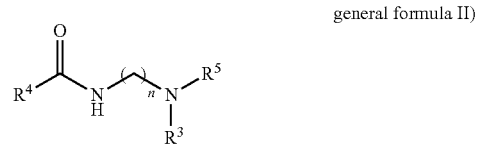

general formula II)

where
$R^4$—CO is selected from an aliphatic, linear or branched acyl radical having 6 to 22 carbon atoms comprising 0, 1, 2 or 3 double bonds, which generally stems from a naturally occurring or synthetically prepared fatty acid,
$R^5$ and $R^3$ are selected from identical or different alkyl radicals, which can optionally carry functional groups such as hydroxy groups, ester groups, amines, amides or other polar substituents, preference being given to unsubstituted hydrocarbon radicals which have at most one or more branches, particular preference being given to hydrocarbon radicals having 1 to 6 carbon atoms, with ethyl and methyl radicals being very particularly preferred according to the invention, and
n=an integer selected from 1 to 10, preferably from 2 to 7, in particular from 2 to 4.

Compounds of general formula II) are usually prepared by amidation of natural or synthetic fatty acids and fatty acid cuts with dialkylaminoamines. Typical examples of such fatty acids are caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, elaeostearic acid, arachic acid, gadoleic acid, behenic acid and erucic acid, and technical-grade mixtures thereof which are produced e.g., during the pressurized cleavage of natural fats and oils, during the reduction of aldehydes from the Roelen oxo synthesis or the dimerization of unsaturated fatty acids.

Particular preference is usually given to the fatty acid cuts which are obtainable from coconut oil or palm oil, with the use of stearic acid generally being particularly preferred.

Depending on the intended use, the formulation according to the invention can comprise the compound of general formula I), II) and optionally Ia) in different ratios.

Preferably, the compounds of general formula I) and optionally Ia) (then in total) to the compounds of general formula II) are present in a weight ratio of 20:1 to 1:20, in particular from 10:1 to 1:10, in the formulation according to the invention.

Depending on the desired effect, the weight ratio can also be varied from 5:1 to 1:5 or from 3:1 to 1:3.

Formulations preferred according to the invention, such as those for treating keratin fibers, in particular human hair, comprise, optionally, in total, 0.1 to 7% by weight, preferably 0.2 to 5% by weight and particularly preferably 0.3 to 3% by weight, of compounds of general formula I) and optionally Ia) and optionally 0.1 to 7% by weight, preferably 0.2 to 5% by weight and particularly preferably 0.3 to 3% by weight, of compounds of general formula II), where the % by weight refer to the total formulation.

Particularly good results can be achieved at the predefined concentrations of 0.2 to 2% by weight. The application of the formulations according to the invention to keratin fibers, in particular to human hair, however, is not limited to the use of the active ingredients in low concentration. It is also possible to use concentrated formulations according to the invention in which the predefined concentrations are 2 to 20% by weight or 3 to 14% by weight, in particular 5 to 12% by weight.

In some embodiments of the present invention, it is preferred if the formulation has a pH from 3.0 to 5.5, preferably 3.5 to 5.0.

The charge of compound I present in the formulation according to the invention must be compensated by corresponding anions; this takes place by means of counteranions present in the formulation according to the invention.

Such counteranions are, for example, the halides, pseudohalides, anions of mineral acids, sulphates, sulphites, hydrogensulphites, sulphonate, alkyl- and arylsulphonates, phosphate, hydrogenphosphates, phosphites, hydrogenphosphites, phosphonites, carboxylates, borates, carbonates, sulphides, hydrogensulphides, lactate, glycolate, formate, acetate, propionate.

These anions are preferably selected from those which are suitable for cosmetic application and are therefore for example nontoxic. Particularly preferably, at least one counteranion to the compound of general formula I) selected from the group of chloride, bromide, iodide, alkyl sulphate, e.g., methyl sulphate, ethyl sulphate, alkylsulphonate, e.g., methylsulphonate, triflate, tosylate, phosphate, sulphate, hydrogensulphate, lactate, glycolate, acetate and citrate, preferably chloride and methyl sulphate, is present.

The compound of general formula I) and the formulations according to the invention can be used according to the invention for treating keratin fibers, in particular for treating hair.

In this connection, preference is given to using those compounds of general formula I) which are described above as preferably being present in the formulations according to the invention.

The use according to the invention leads to the improvement in the conditioning, shine, flexibility, elasticity and/or combability, and also to a reduction in the probability of breakage of the treated fibers and, moreover, it reduces the antistatic forces between the fibers.

The use according to the invention leads to the protection of the fibers against heat.

In the examples listed below, the present invention is described by way of example without any intention of limiting the invention, the scope of application of which arises from the entire description and the claims, to the embodiments specified in the examples.

EXAMPLES

Example 1: Preparation of "1-propanaminium, 2-hydroxy-N-(2-hydroxypropyl)-N,N-dimethyl, diester with plant mixed oil fatty acid, methyl sulphate" (according to the invention)

1120 g (4 mol) of plant mixed oil fatty acid were mixed with 302 g (2.05 mol) of methyldiisopropanolamine and heated to 180° C. with stirring. Water of reaction was distilled off continuously. After the majority of water of reaction had been distilled at atmospheric pressure, vacuum was applied and the acid number of the reaction mixture was reacted down to <7 mg KOH/g. The resulting ester amine was cooled to 60° C. and admixed in portions with 240 g (1.90 mol) of dimethyl sulphate, such that the reaction temperature did not exceed 100° C.

After cooling to room temperature, the total amine number (TAN) and the active content of the finished product were analyzed.

TAN=5.0 mg KOH/g; active content 1.27 meq/g (cationic active content according to Epton).

Example 2: Preparation of "1-propanaminium, 2-hydroxy-N-(2-hydroxypropyl)-N,N-dimethyl, diester with palm fatty acid, methyl sulphate" (not according to the invention)

1020 g (4 mol) of palmitic acid (technical-grade quality, approx. 98% pure) were admixed with 302 g (2.05 mol) of methyldiisopropanolamine and esterified as described under Example 1. The ester amine had an acid number of 5.6 mg KOH/g. This mixture was alkylated with 240 g (1.90 mol) of dimethyl sulphate as described under Example 1.

The TAN of the finished product was determined with 4.8 mg KOH/g, the active content was 1.33 meq/g.

Example 3: Preparation of "1-propanaminium, 2-hydroxy-N-(2-hydroxypropyl)-N,N-dimethyl, diester with tall oil fatty acid, methyl sulphate" (according to the invention)

814 g (2.84 mol) of tall oil fatty acid were mixed with 214 g (1.46 mol) of methyldiisopropanolamine and esterified as described under Example 1. The ester amine had an acid number of 3.2 mg KOH/g. This mixture was alkylated with 168 g (1.33 mol) of dimethyl sulphate as described in Example 1. The TAN of the finished product was determined with 7.3 mg KOH/g, the active content was 1.24 meq/g.

Example 4: Preparation of "1-propanaminium, 2-hydroxy-N-(2-hydroxypropyl)-N,N-dimethyl, diester with erucic acid, methyl sulphate" (according to the invention)

392 g (1.15 mol) of erucic acid were mixed with 99.3 g (0.68 mol) of methyldiisopropanolamine and esterified as described under Example 1. The ester amine had an acid number of 2.2 mg KOH/g. This mixture was alkylated with 72.2 g (0.57 mol) of dimethyl sulphate as described in Example 1. The TAN of the finished product was determined with 4.6 mg KOH/g, the active content was 1.45 meq/g.

Example 5: Preparation of "1-propanaminium, 2-hydroxy-N-(2-hydroxypropyl)-N,N-dimethyl, diester with isostearic acid, methyl sulphate" (according to the invention)

1017 g (3.5 mol) of isostearic acid (technical-grade quality) were admixed with 262 g (1.79 mol) of methyldiisopropanolamine and esterified as described under Example 1. The ester amine had an acid number of 3.4 mg KOH/g. This mixture was alkylated with 209 g (1.66 mol) of dimethyl sulphate as described under Example 1.

The TAN of the finished product was determined with 5.1 mg KOH/g, the active content was 1.26 meq/g.

Example 6: Application Technology of Hair Treatment Compositions Using Example 1 and Example 2 as Well as Commercial Market Products For the applications-related assessment, hair tresses were used which had been predamaged in a standardized manner by means of a bleaching treatment. For this purpose, standard hairdressing products were used. The damage to the hair tresses is described in detail in DE10327871.

For the applications-related assessment, the compound according to the invention from Example 1 was used in a simple cosmetic formulation.

The reference compounds used were the commercially available alkyl quat (INCI) Behentrimonium Chloride (VARISOFT® BT 85 Pellets, Evonik Industries) and the commercially available ester quat (INCI) DistearoylethylDimonium Chloride (VARISOFT® EQ 65 Pellets, Evonik Industries), as well as the compound dimethyldi(palmitoyloxyisopropyl)ammonium chloride.

The application properties upon use in hair rinses were tested in the following formulations (Tab. 1):

The composition of the test formulations were deliberately chosen to be simple in order to avoid the test results being influenced by (normally present) formulation constituents. Besides the specified ingredients and/or instead of the specified ingredients, formulations according to the invention can also comprise further ingredients. In particular, the combination with further ingredients can lead to a synergistic improvement in the case of the described effects.

The hair was pretreated using a shampoo formulation (Tab. 2) which comprises no conditioners.

TABLE 2

| Shampoo formulation for the pretreatment of the hair tresses. | |
| --- | --- |
| Texapon NSO ®, 28% strength, Cognis (INCI: SodiumLaureth Sulphate) | 42.9% |
| NaCl | 3% |
| Water, demineralized | ad 100.0 |

Standardized treatment of predamaged hair tresses with conditioning samples: The hair tresses predamaged as described above were washed with the shampoo formulation from Tab. 2.

Here, the hair tresses were wetted under running warm water. The excess water was gently squeezed out by hand, then the shampoo was applied and worked gently into the hair for 1 min (0.5 ml/2 g hair tress). The hair tress was rinsed for 30 s under running warm water. This procedure was repeated once more except that final rinsing was for 1 min.

Then, directly after washing, the hair tresses were conditioned with the hair rinse formulations from Tab. 1.

Here, the rinse was applied and gently worked into the hair (0.5 ml/2 g hair tress). After a residence time of 1 min, the hair was rinsed for a) 1 min or for b) 3 min.

Before the sensory assessment, the hair was dried for at least 12 h in the air at 50% humidity and 25° C.

TABLE 1

| Hair rinse formulation for testing the hair conditioning properties | | | | | | | | |
| --- | --- | --- | --- | --- | --- | --- | --- | --- |
| | Formulation examples | | | | | | | |
| | C0a | 1a | V2a | V3a | V4a | 5a | 6a | 7a |
| TEGINACID ® C, Evonik Industries (INCI: Ceteareth-25) | 0.5% | 0.5% | 0.5% | 0.5% | 0.5% | 0.5% | 0.5% | 0.5% |
| TEGO ® Alkanol 18, Evonik Industries (INCI: Stearyl alcohol) | 4% | 4% | 4% | 4% | 4% | 4% | 4% | 4% |
| Example 1 (100%) | | 1.5% | | | | | | |
| Example 2 (80% in isopropanol) | | | 1.9% | | | | | |
| Example 3 | | | | | | 1.5% | | |
| Example 4 | | | | | | | 1.5% | |
| Example 5 | | | | | | | | 1.5% |
| VARISOFT ® EQ 65 Pellets (65% strength in C16 fatty alcohol), Evonik Industries (INCI: DistearoylethylDimonium Chloride, Cetearyl Alcohol) | | | | 2.3% | | | | |
| VARISOFT ® BT 85, (85% strength in isopropanol), Evonik Industries (INCI: Behentrimonium Chloride) | | | | | 1.76% | | | |
| Water, demineralized | | | | ad 100.0 | | | | |
| Citric acid | | | | ad pH 4.0 | | | | |

Assessment Criteria:

The sensory evaluations were made according to grades which were awarded on a scale from 1 to 5, with 1 being the poorest evaluation and 5 the best evaluation. The individual test criteria were each given their own evaluation.

The test criteria were:
Wet combability, wet feel, dry combability, dry feel, appearance/shine.

The tables below compare the results of the sensory assessment of the treatment of the hair tresses carried out as described above with a) 1 min rinsing time and for b) 3 min rinsing time with the formulation 1a according to the invention, the comparison formulations V2a, V3a and V4a and the control formulation C0a (control without test substance), and for aa) 1 min rinsing time and for bb) 3 min rinsing time with the formulation 7a according to the invention, the comparison formulations V2a, V3a and V4a and the control formulation C0a (control without test substance).

a) 1 min rinsing time

TABLE 3a

Results of the conditioning of hair with 1 min rinsing time

|  | Wet combability | Wet feel | Dry combability | Dry feel |
|---|---|---|---|---|
| Formulation 1a according to the invention | 5 | 5 | 5 | 5 |
| Comparison formulation 2a | 3.5 | 3.5 | 3.5 | 3.5 |
| Comparison formulation 3a | 3.5 | 3.5 | 4 | 3.5 |
| Comparison formulation 4a | 4.5 | 4.5 | 4.5 | 4.5 |
| Control C0a | 2 | 2 | 3 | 2.5 | b) 3 min rinsing time

TABLE 3b

Results of the conditioning of hair with 3 min rinsing time

|  | Wet combability | Wet feel | Dry combability | Dry feel |
|---|---|---|---|---|
| Formulation 1a according to the invention | 5 | 5 | 5 | 5 |
| Comparison formulation 2a | 3.0 | 3.0 | 3.5 | 3.5 |
| Comparison formulation 3a | 3.5 | 3.5 | 4 | 3 |
| Comparison formulation 4a | 4 | 4 | 4 | 4 |
| Control C0a | 2 | 2 | 3 | 2.5 |

The results in Table 3a show that the formulation 1a according to the invention has very good conditioning properties with 1 min rinsing time, which are significantly superior to the comparison formulations V2a, V3a and V4a.

The results in Table 3b show that the formulation 1a according to the invention has even more markedly improved conditioning properties with 3 min rinsing time than after 1 min than the comparison formulations V2a, V3a and V4a. The comparison formulation V4a comprises, as conditioning compound, VARISOFT®BT 85 (85% strength in isopropanol, Evonik Industries, INCI: Behentrimonium Chloride), an alkyl quat which is known for its very good conditioning properties even in the case of long rinsing times. The comparison formulation V3a comprises, as conditioning compound, VARISOFT® EQ 65Pellets (65% strength in C 16 fatty alcohol, Evonik Industries, INCI: DistearoylethylDimonium Chloride, Cetearyl Alcohol), an ester quat which has very good conditioning properties in the case of a 1 min rinsing time (see Tab. 3a), but exhibits considerably poorer conditioning in the case of a 3 min rinsing time.

aa) 1 min rinsing time

TABLE 3c

Results of the conditioning of hair with 1 min rinsing time

|  | Wet combability | Wet feel | Dry combability | Dry feel |
|---|---|---|---|---|
| Formulation 7a according to the invention | 5 | 5 | 5 | 5 |
| Comparison formulation 2a | 3.5 | 3.5 | 3.5 | 3.5 |
| Comparison formulation 3a | 3.5 | 3.5 | 4 | 4 |
| Comparison formulation 4a | 4.5 | 4.5 | 4.5 | 4.5 |
| Control C0a | 2 | 2 | 3 | 2.5 | bb) 3 min rinsing time

TABLE 3d

Results of the conditioning of hair with 3 min rinsing time

|  | Wet combability | Wet feel | Dry combability | Dry feel |
|---|---|---|---|---|
| Formulation 7a according to the invention | 5 | 5 | 5 | 5 |
| Comparison formulation 2a | 3.0 | 3.0 | 3.5 | 3.5 |
| Comparison formulation 3a | 3.5 | 3.0 | 3.5 | 3.5 |
| Comparison formulation 4a | 4 | 4 | 4 | 4 |
| Control C0a | 2 | 2 | 3 | 2.5 |

The results in Table 3c show that the formulation 7a according to the invention has very good conditioning properties in the case of a 1 min rinsing time which are significantly superior to the comparison formulations V2a, V3a and V4a.

The results in Table 3d show that the formulation 7a according to the invention has even more markedly improved conditioning properties in the case of a 3 min rinsing time than after 1 min than the comparison formulations V2a, V3a and V4a. The comparison formulation V4a comprises, as conditioning compound, VARISOFT®BT 85 (85% strength in isopropanol, Evonik Industries, INCI: Behentrimonium Chloride), an alkyl quat which is known for its very good conditioning properties even in the case of long rinsing times. The comparison formulation V3a comprises, as conditioning compound, VARISOFT® EQ 65Pellets (65% strength in C 16 fatty alcohol, Evonik Industries, INCI: DistearoylethylDimonium Chloride, Cetearyl Alcohol), an ester quat which has very good conditioning properties in the case of a 1 min rinsing time (see Tab. 3a), but exhibits considerably poorer conditioning in the case of a 3 min rinsing time.

Example 7: Influence of the Compounds According to the Invention on Combing Forces of Hair Experimental Conditions:
Instrument: Diastron MTT 175
Measurement distance: 20 cm
Combing rate: 2000 mm/min Carrying out the combing force measurement after treatment with the test formulation: Points 3-5 were repeated.

The combability (%) was then calculated before and after treatment with the test formulation.

Test Formulations Used:

The combing forces when used in hair rinses were tested in the following formulations (Tab. 4):

TABLE 4

Hair rinse formulations for testing the hair conditioning properties

| | Formulation examples | | | | | | | |
|---|---|---|---|---|---|---|---|---|
| | C0b | 1b | V2b | V3b | V4b | 5b | 6b | 7b |
| TEGINACID C, Evonik Industries (INCI: Ceteareth-25) | 0.5% | 0.5% | 0.5% | 0.5% | 0.5% | 0.5% | 0.5% | 0.5% |
| TEGO Alkanol 18, Evonik Industries (INCI: Stearyl alcohol) | 4% | 4% | 4% | 4% | 4% | 4% | 4% | 4% |
| Example 1 (100%) | | 1% | | | | | | |
| Example 2 (80% strength in isopropanol) | | | 1.25% | | | | | |
| Example 3 | | | | | | 1% | | |
| Example 4 | | | | | | | 1% | |
| Example 5 | | | | | | | | 1% |
| Varisoft EQ 65 Pellets (65% strength in C16 fatty alcohol), Evonik Industries (INCI: Distearoylethyl-Dimonium Chloride, Cetearyl Alcohol) | | | | 1.53% | | | | |
| VARISOFT BT 85, (85% strength in isopropanol), Evonik Industries (INCI: Behentrimonium Chloride) | | | | | 1.18% | | | |
| Water, demineralized | | | | ad 100.0 | | | | |
| Citric acid | | | | ad pH 4.0 | | | | |

Hair tresses used: length=23 cm; width=1.5 cm; weight=2 g
Measurement conditions: T=22° C.

The hair tresses were measured with a residual moisture of 60%, determined by weight determination.

European, undamaged, dark brown hair was used for the experiments. To carry out the combing force measurements, this hair was damaged by means of perming in the laboratory in accordance with standard conditions:

1.) 4 g perming solution/g of hair, leave to act for 15 min, rinse out for 2 min under running tap water (T=35° C.) (Perming solution: Universal perm, Basler) 2.) 4 g of neutralizer (1 part neutralizing solution+3 parts water)/g of hair, allow to act for 10 min, rinse out for 2 min. (Neutralizer solution: foam neutralizer concentrate, Basler)

Carrying out the combing force measurement before the treatment with the test formulation:

The predamaged hair tresses were climatized overnight.
3.) The hair tress was dipped for 1 min in a buffer solution (Na citrate, pH=6).
4.) The hair tress was precombed by hand until no change in combing resistance was ascertained.
5.) The hair tress was clamped in the instrument and the first combing force measurement was carried out. The measurement was repeated a total of 10 times.

Treatment of the Tresses:

0.5 g of the respective test formulation was used per hair tress (2 g hair/0.5 g solution). The formulation was massaged into the hair for 30 sec and then left on for 5 min, then rinsed off under running tap water for 1 min or 3 min.

FIGS. 1-4 compare the results of the combing force measurements of the experiments carried out as described above in the case of a) 1 min rinsing time and in the case of b) 3 min rinsing time with the formulation Ib according to the invention, the comparison formulations V3b and V4b and the control formulation C0b (control without test substance).

The results in FIG. 1 show that the formulation Ib according to the invention in the case of a 1 min rinsing time has a more marked reduction in the combing forces than the comparison formulation V3b. The results in FIG. 1 also show that the formulation Ib according to the invention in the case of a 3 min rinsing time has a more marked reduction in the combing forces than the comparison formulation V3b. The comparison formulation V3b comprises, as conditioning compound, VARISOFT® EQ 65 Pellets (65% strength in C 16 fatty alcohol, Evonik Industries, INCI: DistearoylethylDimonium Chloride, Cetearyl Alcohol), an ester quat.

Figure 2:
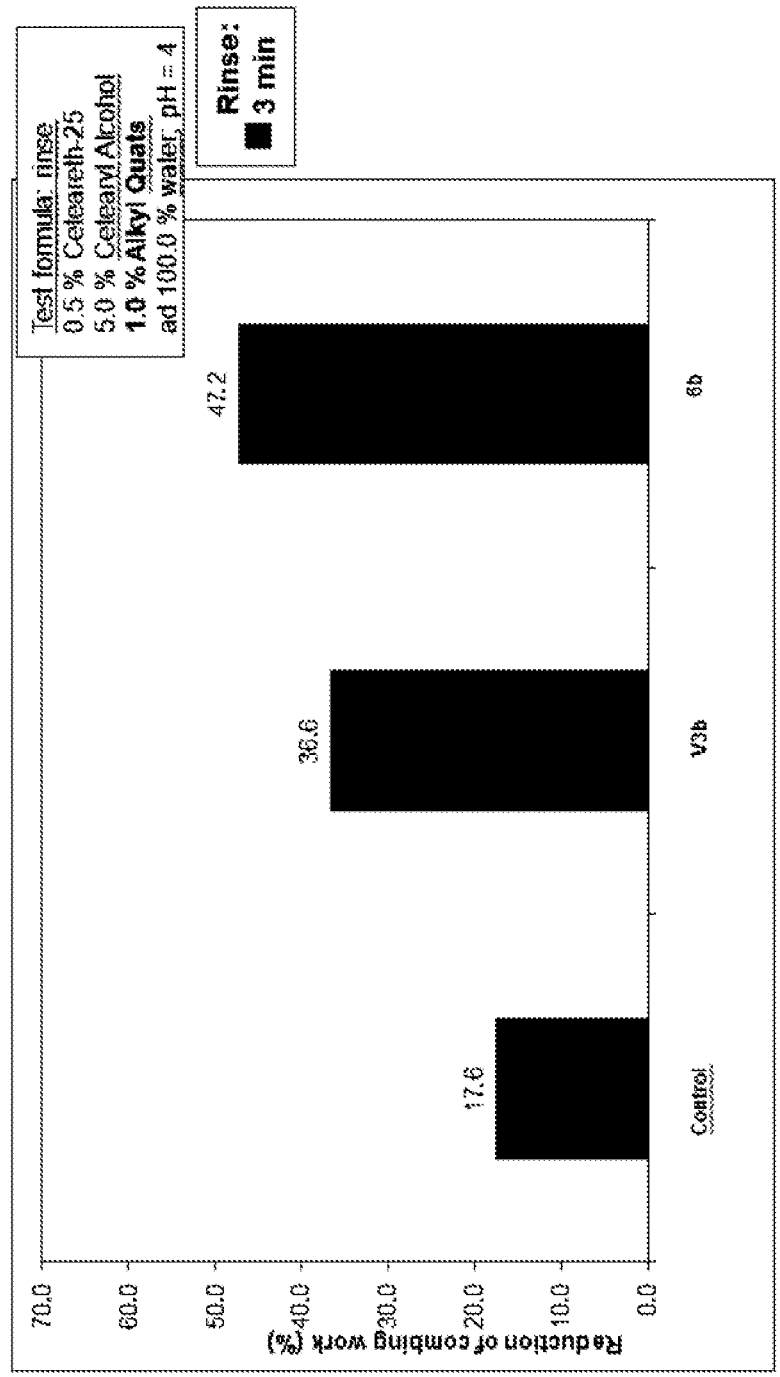
FIG. 2 illustrates the Combing force measurements comparison of formulation 6b with V3b.

The results in FIG. 2 show that the formulation 6b according to the invention in the case of a 3 min rinsing time has a more marked reduction in the combing forces than the comparison formulation V3b.

The comparison formulation V3b comprises, as conditioning compound, VARISOFT® EQ 65 Pellets (65% strength in C 16 fatty alcohol, Evonik Industries, INCI: DistearoylethylDimonium Chloride, Cetearyl Alcohol), an ester quat.

Figure 3:
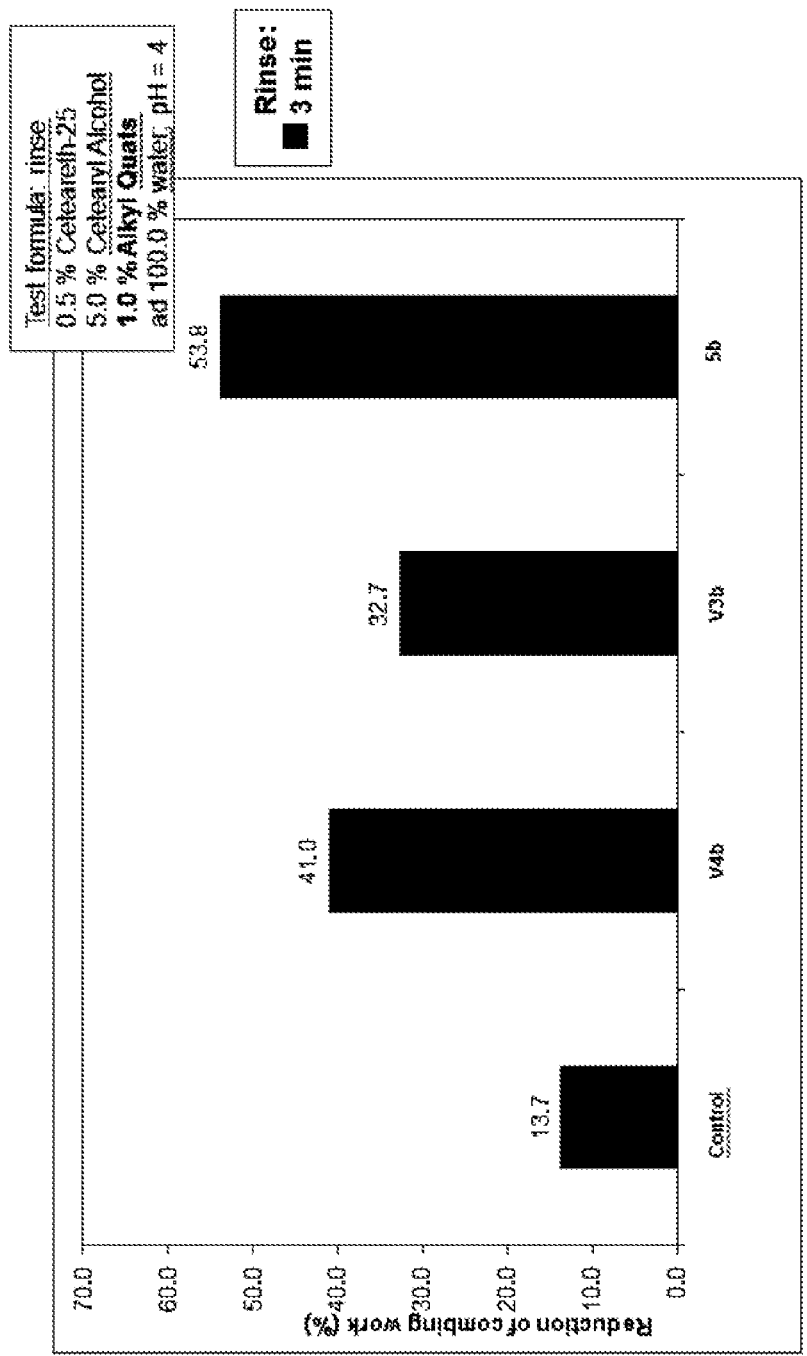
FIG. 3 illustrates the combing force measurements comparison of formulation 5b with V3b and V4b.

The results in FIG. 3 show that the formulation 5b according to the invention in the case of a 3 min rinsing time has a more marked reduction in the combing forces than the comparison formulations V3b and V4b.

The comparison formulation V3b comprises, as conditioning compound, VARISOFT® EQ 65 Pellets (65% strength in C 16 fatty alcohol, Evonik Industries, INCI: DistearoylethylDimonium Chloride, Cetearyl Alcohol), an ester quat. The comparison formulation V4b comprises, as conditioning compound, VARISOFT® BT 85 (85% strength in isopropanol, Evonik Industries, INCI: Behentrimonium Chloride), an alkyl quat which is known for its considerable reduction in the combing forces even in the case of long rinsing times.

Figure 4:
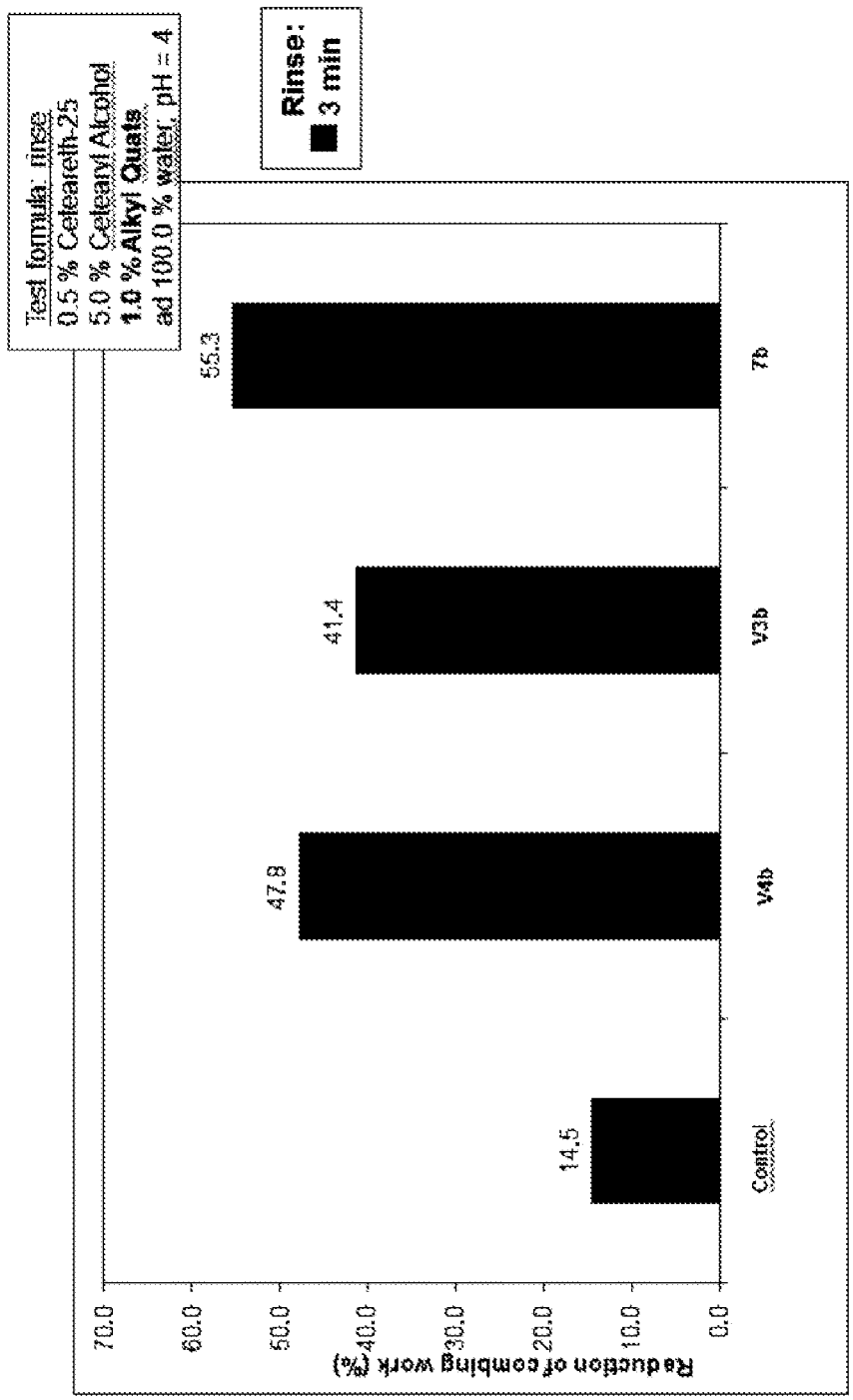
FIG. 4 illustrates the combing force measurements comparison of formulation 7b with V3b and V4b.

The results in FIG. 4 show that the formulation 7b according to the invention in the case of a 3 min rinsing time has a more marked reduction in the combing forces than the comparison formulations V3b and V4b.

The comparison formulation V3b comprises, as conditioning compound, VARISOFT® EQ 65 Pellets (65% strength in C 16 fatty alcohol, Evonik Industries, INCI: DistearoylethylDimonium Chloride, Cetearyl Alcohol), an ester quat. The comparison formulation V4b comprises, as conditioning compound, VARISOFT® BT 85 (85% strength in isopropanol, Evonik Industries, INCI: Behentrimonium Chloride), an alkyl quat which is known for its considerable reduction in the combing forces even in the case of long rinsing times.

Example 8: Antistatic Finishing of Keratin Fibers

To test the antistatic behavior, the shadow silhouette method was used.

The pretreated hair tresses described above, a plastic comb, a spotlight and a projection field marked with concentric semicircles were used.

The experiments were carried out under standardized climatic conditions.

The hair tress was hung up at a distance of 15 cm from the projection field. The spotlight was positioned at a distance of 145 cm from the hair tress so that a shadow fell on the projection field.

The hair tress was then combed five times in succession using the comb. The electrostatic charging was measured via the shadow silhouette by marking the two outer points of the shadow and determining the distance between them. The smaller the shadow area, the more effective the antistatic effect.

Result:

| Formulation | Distance |
|---|---|
| C0a | 15 cm |
| 1a | 5 cm |

EXAMPLE FORMULATIONS

Formulation Example 1) Pearlized Shampoo

| | |
|---|---|
| TEXAPON® NSO, Cognis, 28% strength (INCI: SodiumLaureth Sulphate) | 32.25% |
| Example 1 according to the invention | 0.25% |
| Perfume | 0.25% |
| Water | 55.25% |
| TEGO®Betain F 50, Evonik Industries AG, 38% strength (INCI: CocamidopropylBetaine) | 8.00% |
| TEGO® Pearl N 300 Evonik Industries AG (INCI: Glycol Distearate; Laureth-4; CocamidopropylBetaine) | 2.00% |
| ANTIL® 171 Evonik Industries AG (INCI: PEG-18 Glyceryl Oleate/Cocoate) | 1.50% |
| NaCl | 0.50% |
| Preservative | q.s. |

Formulation Example 2) Rinse-Off Conditioner

| | |
|---|---|
| Water | 92.0% |
| TEGINACID® C, Evonik Industries AG (INCI: Ceteareth-25) | 0.5% |
| Example 1 according to the invention | 2.50% |
| TEGO®Alkanol 1618, Evonik Industries AG (INCI: Cetearyl Alcohol) | 5.00% |
| Preservative, Perfume | q.s. |

Formulation Example 3) Rinse-Off Conditioner

| | |
|---|---|
| Water | 91.0% |
| Example 1 according to the invention | 2.00% |
| VARISOFT® BT 85, Evonik Industries AG (INCI: Behentrimonium Chloride) | 2.00% |
| TEGO®Alkanol 1618, Evonik Industries AG (INCI: Cetearyl Alcohol) | 5.00% |
| Preservative, Perfume | q.s. |

Formulation Example 4) Rinse-Off Conditioner

| | |
|---|---|
| Water | 90.20% |
| Example 1 according to the invention | 2.00% |
| VARISOFT® EQ 65, Evonik Industries AG (INCI: DistearoylDimonium Chloride, Cetearyl Alcohol) | 2.00% |
| TEGO®Alkanol 1618, Evonik Industries AG (INCI: Cetearyl Alcohol) | 5.80% |
| Preservative, Perfume | q.s. |

Formulation Example 5) Rinse-Off Conditioner

| | |
|---|---|
| Water | 89.20% |
| TEGINACID® C, Evonik Industries AG (INCI: Ceteareth-25) | 0.5% |
| VARISOFT® EQ 65, Evonik Industries AG (INCI: DistearoylDimonium Chloride, Cetearyl Alcohol) | 2.00% |
| Example 1 according to the invention | 2.00% |
| ABIL® Quat 3272, Evonik Industries AG (INCI: Quaternium-80) | 1.30% |
| TEGO®Alkanol 1618, Evonik Industries AG (INCI: Cetearyl Alcohol) | 5.00% |
| Preservative, Perfume | q.s. |

Formulation Example 6) Rinse-Off Conditioner

| | |
|---|---|
| TEGINACID ® C, Evonik Industries AG (INCI: Ceteareth-25) | 0.50% |
| TEGO ®Alkanol 16, Evonik Industries AG (INCI: Cetyl Alcohol) | 2.00% |
| TEGO ® Amid S 18, Evonik Industries AG (INCI: StearamidopropylDimethylamine) | 1.00% |
| Example 1 according to the invention | 1.50% |
| PropyleneGlycol | 2.00% |
| CitricAcid Monohydrate | 0.30% |
| Water | 92.70% |
| Preservative, Perfume | q.s. |

Formulation Example 7) Rinse-Off Conditioner

| | |
|---|---|
| TEGINACID ® C, Evonik Industries AG (INCI: Ceteareth-25) | 0.50% |
| TEGO ®Alkanol 16, Evonik Industries AG (INCI: Cetyl Alcohol) | 5.00% |
| TEGOSOFT ® DEC, Evonik Industries AG (INCI: Diethylhexyl Carbonate) | 1.00% |
| Example 1 according to the invention | 1.50% |
| Water | 89.20% |
| TEGO ® Cosmo C 100 Evonik Industries AG (INCI: Creatine) | 0.50% |
| PropyleneGlycol | 2.00% |
| CitricAcid Monohydrate | 0.30% |
| Preservative, Perfume | q.s. |

Formulation Example 8) Leave-in Conditioner Spray

| | |
|---|---|
| Lactic Acid, 80% | 0.40% |
| Water | 95.30% |
| Example 1 according to the invention | 1.20% |
| TEGIN ® G 1100 Pellets, Evonik Industries AG (INCI: GlycolDistearate) | 0.60% |
| TEGO ® Care PS, Evonik Industries AG (INCI: Methyl Glucose Sesquistearate) | 1.20% |
| TEGOSOFT ® DEC, Evonik Industries AG (INCI: Diethylhexyl Carbonate) | 1.30% |
| Preservative, Perfume | q.s. |

Formulation Example 9) Leave-in Conditioner Spray

| | |
|---|---|
| Lactic Acid, 80% | 0.40% |
| Water | 95.30% |
| TEGO ® Amid S 18, Evonik Industries AG (INCI: StearamidopropylDimethylamine) | 1.20% |
| Example 1 according to the invention | 0.30% |
| TEGIN ® G 1100 Pellets, Evonik Industries AG (INCI: GlycolDistearate) | 0.90% |
| TEGO ® Care PS, Evonik Industries AG (INCI: Methyl Glucose Sesquistearate) | 1.60% |
| TEGOSOFT ® DEC, Evonik Industries AG (INCI: Diethylhexyl Carbonate) | 0.30% |
| Preservative, Perfume | q.s. |

Formulation Example 10) Leave-in Conditioner Spray

| | |
|---|---|
| TAGAT ® CH-40, Evonik Industries AG (INCI: PEG-40 Hydrogenated Castor Oil) | 2.20% |
| Ceramide VI, Evonik Industries AG (INCI: Ceramide 6 II) | 0.05% |
| Perfume | 0.20% |
| Water | 90.95% |
| Example 1 according to the invention | 0.30% |
| LACTIL ® Evonik Industries AG (INCI: Sodium Lactate; Sodium PCA; Glycine; Fructose; Urea; Niacinamide; Inositol; Sodium benzoate; Lactic Acid) | 2.00% |
| TEGO ®Betain F 50 Evonik Industries AG 38% (INCI: CocamidopropylBetaine) | 2.30% |
| Citric Acid (10% in water) | 2.00% |

Formulation Example 11) Leave-in Conditioner Foam

| | |
|---|---|
| Example 1 according to the invention | 0.30% |
| TAGAT ® CH-40, Evonik Industries AG (INCI: PEG-40 Hydrogenated Castor Oil) | 1.0% |
| Perfume | 0.30% |
| TEGO ®Betain 810, Evonik Industries AG (INCI: Capryl/CapramidopropylBetaine) | 2.00% |
| Water | 94.00% |
| TEGO ® Cosmo C 100, Evonik Industries AG (INCI: Creatine) | 0.50% |
| TEGOCEL ® HPM 50, Evonik Industries AG (INCI: Hydroxypropyl Methylcellulose) | 0.30% |
| VARISOFT ® 300, Evonik Industries AG (INCI: Cetrimonium Chloride) | 1.0% |
| LACTIL ® Evonik Industries AG (INCI: Sodium Lactate; Sodium PCA; Glycine; Fructose; Urea; Niacinamide; Inositol; Sodium benzoate; Lactic Acid) | 0.50% |
| Citric Acid, 30% | 0.10% |
| Preservative | q.s. |

Formulation Example 12) Strong Hold Styling Gel

| | |
|---|---|
| TEGO ®Carbomer 141, Evonik Industries AG (INCI: Carbomer) | 1.20% |
| Water | 66.70% |
| NaOH, 25% | 2.70% |
| PVP/VA W-735, ISP (INCI: PVP/VA Copolymer) | 16.00% |
| Example 1 according to the invention | 0.30% |
| AlcoholDenat. | 10.50% |
| TAGAT ® O 2 V, Evonik Industries AG (INCI: PEG-20 Glyceryl Oleate) | 2.00% |
| Perfume | 0.30% |
| ABIL ® B 88183, Evonik Industries AG (INCI: PEG/PPG-20/6 Dimethicone) | 0.30% |
| Preservative | q.s. |

Formulation Example 13) Bodycare Composition

| | |
|---|---|
| TEXAPON ® NSO, Cognis, 28% strength (INCI: SodiumLaureth Sulphate) | 30.00% |
| TEGOSOFT ® PC 31, Evonik Industries AG (INCI: Polyglyceryl-3 Caprate) | 0.70% |
| Example 1 according to the invention | 0.30% |
| Perfume | 0.30% |
| Water | 53.90% |

-continued

| | |
|---|---|
| TEGOCEL ® HPM 4000, Evonik Industries AG (INCI: Hydroxypropyl Methylcellulose) | 0.30% |
| REWOTERIC ® AM C, Evonik Industries AG, 32% strength (INCI: SodiumCocoamphoacetate) | 10.00% |
| CitricAcid Monohydrate | 0.50% |
| REWODERM ® LI S 80, Evonik Industries AG (INCI: PEG-200 HydrogenatedGlycerylPalmate; PEG-7 GlycerylCocoate) | 2.00% |
| TEGO ® Pearl N 300, Evonik Industries AG (INCI: Glycol Distearate; Laureth-4; CocamidopropylBetaine) | 2.00% |

Formulation Example 14) Mild Foam Bath

| | |
|---|---|
| TEXAPON ® NSO, Cognis, 28% strength (INCI: Sodium LaurethSulphate) | 27.00% |
| REWOPOL ® SB FA 30, Evonik Industries AG, 40% strength (INCI: DisodiumLaurethSulphosuccinate) | 12.00% |
| TEGOSOFT ® LSE 65 K SOFT, Evonik Industries AG (INCI: Sucrose Cocoate) | 2.00% |
| Water | 39.00% |
| REWOTERIC ® AM C, Evonik Industries AG, 32% strength (INCI: SodiumCocoamphoacetate) | 13.00% |
| Example 1 according to the invention | 0.40% |
| Citric Acid (30% in water) | 3.00% |
| ANTIL ® 171 Evonik Industries AG (INCI: PEG-18 GlycerylOleate/Cocoate) | 1.60% |
| TEGO ® Pearl N 300 Evonik Industries AG (INCI: Glycol Distearate; Laureth-4; CocamidopropylBetaine) | 2.00% |

Formulation Example 15) Rinse-Off Conditioner

| | |
|---|---|
| Water | 89.20% |
| Example 1 according to the invention | 3.00% |
| ABIL ® OSW 5, Evonik Industries AG (INCI: Cyclopentasiloxane; Dimethiconol) | 1.80% |
| TEGO ®Alkanol 1618, Evonik Industries AG (INCI: Cetearyl Alcohol) | 6.00% |
| Preservative, Perfume | q.s. |

Formulation Example 16) Rinse-Off Conditioner

| | |
|---|---|
| Water | 89.20% |
| TEGINACID ® C, Evonik Industries AG (INCI: Ceteareth-25) | 0.5% |
| VARISOFT ® EQ 65, Evonik Industries AG (INCI: DistearylDimonium Chloride, Cetearyl Alcohol) | 1.50% |
| Example 1 according to the invention | 2.00% |
| ABIL ® Soft AF 100, Evonik Industries AG (INCI: Methoxy PEG/PPG-7/3 AminopropylDimethicone) | 1.00% |
| TEGO ®Alkanol 1618, Evonik Industries AG (INCI: Cetearyl Alcohol) | 5.80% |
| Preservative, Perfume | q.s. |

Formulation Example 17) Rinse-Off Conditioner

| | |
|---|---|
| Water | 91.50% |
| TEGINACID ® C, Evonik Industries AG (INCI: Ceteareth-25) | 0.5% |
| Example 1 according to the invention | 2.00% |
| SF 1708, Momentive (INCI: Amodimethicone) | 1.00% |
| TEGO ®Alkanol 1618, Evonik Industries AG (INCI: Cetearyl Alcohol) | 5.00% |
| Preservative, Perfume | q.s. |

Formulation Example 18) 2 in 1 Shampoo & Intensive Conditioner

| | |
|---|---|
| Water | 28.00% |
| Jaguar C-162 (HydroxypropylGuarHydroxypropyltrimonium Chloride) | 0.5% |
| VARISOFT ®BT 85, Evonik Industries AG (INCI: Behentrimonium Chloride) | 0.50% |
| Example 1 according to the invention | 0.50% |
| TEGO ®Alkanol 1618, Evonik Industries AG (INCI: Cetearyl Alcohol) | 1.00% |
| TEGIN ® G 1100 Pellets, Evonik Industries AG (INCI: GlycolDistearate) | 0.80% |
| SodiumLaureth Sulphate, 28% | 39.0% |
| Petrolatum | 1.0% |
| ABIL ®T-Quat 60, Evonik Industries AG (INCI: Silicone Quaternium-22) | 1.3% |
| REWOTERIC ® AM C, Evonik Industries AG (INCI: SodiumCocoamphoacetate | 17.50% |
| Citric Acid (20%) | 6.3% |
| ANTIL ® SPA 80, Evonik Industries AG (INCI: Isostearamide MIPA; GlycerylLaurate) | 2.20% |
| NaCl | 1.0% |
| REWODERM ® LI S 80, Evonik Industries AG (INCI: PEG-200 HydrogenatedGlycerylPalmate; PEG-7 GlycerylCocoate) | 1.0% |
| Preservative, Perfume | q.s. |

Formulation Example 19: Pet Care—Conditioner

| | |
|---|---|
| TEGO ®Alkanol 1618, Evonik Industries AG (INCI: Cetearyl Alcohol) | 4.0% |
| TEGINACID ® C, Evonik Industries AG (INCI: Ceteareth-25) | 0.5% |
| VARISOFT ®BT 85, Evonik Industries AG (INCI: Behentrimonium Chloride) | 2.0% |
| Example 1 according to the invention | 1.0% |
| TEGIN ® M, Evonik Industries AG (INCI: GlycerylStearate) | 0.5% |
| Water | 93.0% |
| Preservative, Perfume | q.s. |

Formulation Example 20: In-Shower Hair and Body Conditioner (O/W Emulsion)

| | |
|---|---|
| ABIL ® Soft AF 100, Evonik Industries AG (INCI: Methoxy PEG/PPG-7/3 AminopropylDimethicone) | 0.5% |
| Example 1 according to the invention | 1.0% |
| VARISOFT ®BT 85, Evonik Industries AG (INCI: Behentrimonium Chloride) | 0.5% |
| TEGO ®Alkanol 16, Evonik Industries AG (INCI: Cetyl Alcohol) | 2.0% |
| *Simmondsia Chinensis* (Jojoba) Seed Oil | 0.5% |
| Water | 93.5% |
| Glycerol | 2.0% |
| Panthenol | 0.2% |
| Preservative, Perfume | q.s. |

Formulation Example 21: Hot Oil Treatment

| | |
|---|---|
| Water | 96.5% |
| Polyquaternium-10 | 1.0% |
| Hydroxyethylcellulose | 0.5% |
| Example 1 according to the invention | 1.0% |
| VARISOFT ®BT 85, Evonik Industries AG (INCI: Behentrimonium Chloride) | 1.0% |
| Lauramide DEA | 1.0% |
| Citric Acid, 30% | q.s. |
| Preservative, Perfume | q.s. |

Formulation Example 22: Strong Conditioning Hair Rinse for Damaged Hair

| | |
|---|---|
| VARISOFT ®BT 85, Evonik Industries AG (INCI: Behentrimonium Chloride) | 0.5% |
| Example 1 according to the invention | 0.5% |
| COSMOFERM ®Mix III, Evonik Industries AG (INCI: Isocetyl Alcohol; Ceramide NP; Cetyl Alcohol) | 2.0% |
| TEGINACID ® C, Evonik Industries AG (INCI: Ceteareth-25) | 0.5% |
| ABIL ® Soft AF 100, Evonik Industries AG (INCI: Methoxy PEG/PPG-7/3 AminopropylDimethicone) | 0.3% |
| TEGO ®Alkanol 16, Evonik Industries AG (INCI: Cetyl Alcohol) | 2.0% |
| TEGIN ® M, Evonik Industries AG (INCI: GlycerylStearate) | 1.0% |
| ABIL ® OSW 5, Evonik Industries AG (INCI: Cyclopentasiloxane; Dimethiconol) | 7.5% |
| Water | 86.2% |
| Preservative, Perfume | q.s. |

Formulation Example 23: Conditioning Hair Rinse for Coloured Hair

| | |
|---|---|
| TEGIN ® M, Evonik Industries AG (INCI: GlycerylStearate) | 2.0% |
| TEGO ®Alkanol 1618, Evonik Industries AG (INCI: Cetearyl Alcohol) | 3.0% |
| TEGO ®Amid S 18, Evonik Industries AG (INCI: StearamidopropylDimethylamine) | 0.7% |
| VARISOFT ®BT 85, Evonik Industries AG (INCI: Behentrimonium Chloride) | 0.8% |
| Example 1 according to the invention | 0.8% |
| VARISOFT ®W 575 PG, Evonik Industries AG (INCI: Quaternium-87) | 0.9% |
| Water | 90.9% |
| 1,2-Propylene glycol (PropyleneGlycol) | 1.0% |
| Citric Acid (20%) | 0.7% |
| Preservative, Perfume | q.s. |

Formulation Example 24: Conditioning Hair Rinse

| | |
|---|---|
| TEGO ®Alkanol 1618, Evonik Industries AG (INCI: Cetearyl Alcohol) | 5.0% |
| TEGO ®Care 450 Evonik Industries AG (INCI: Polyglyceryl-3 Methylglucose Distearate) | 1.0% |
| Example 1 according to the invention | 1.0% |
| Water | 92.55% |
| Preservative | 0.45% |

Formulation Example 25: Conditioning Hair Rinse

| | |
|---|---|
| TEGO ®Alkanol 1618, Evonik Industries AG (INCI: Cetearyl Alcohol) | 5.0% |
| TEGO ® Care CG 90, Evonik Industries AG (INCI: Cetearyl Glucoside) | 1.0% |
| Example 1 according to the invention | 1.0% |
| Water | 92.55% |
| Preservative | 0.45% |

Formulation Example 26: Conditioning Hair Rinse

| | |
|---|---|
| TEGO ®Alkanol 1618, Evonik Industries AG (INCI: Cetearyl Alcohol) | 5.0% |
| TEGO ® Care PSC 3, Evonik Industries AG (INCI: Polyglyceryl-3 Dicitrate/Stearate) | 1.0% |
| Example 1 according to the invention | 1.0% |
| Water | 92.55% |
| Preservative | 0.45% |

Formulation Example 27: Conditioning Hair Rinse

| | |
|---|---|
| TEGO ®Alkanol 1618, Evonik Industries AG (INCI: Cetearyl Alcohol) | 5.0% |
| TEGO ® Acid S 40 P, Evonik Industries AG (INCI: PEG-40 Stearate) | 1.0% |
| Example 1 according to the invention | 1.0% |
| Water | 92.55% |
| Preservative | 0.45% |

Formulation Example 28: Conditioning Hair Rinse

| | |
|---|---|
| TEGO ®Alkanol 1618, Evonik Industries AG (INCI: Cetearyl Alcohol) | 5.0% |
| ABIL ® Care 85, Evonik Industries AG (INCI: Bis-PEG/PPG-16/16 PEG/PPG-16/16 Dimethicone; Caprylic/Capric Triglyceride) | 1.0% |
| Example 1 according to the invention | 1.0% |
| Water | 92.55% |
| Preservative | 0.45% |

Formulation Example 29: Conditioning Hair Rinse

| | |
|---|---|
| TEGO ®Alkanol 1618, Evonik Industries AG (INCI: Cetearyl Alcohol) | 5.0% |
| ABIL ® Care XL 80, Evonik Industries AG (INCI: Bis-PEG/PPG-20/5 PEG/PPG-20/5 Dimethicone; Methoxy PEG/PPG-25/4 Dimethicone; Caprylic/Capric Triglyceride) | 1.0% |
| Example 1 according to the invention | 1.0% |
| Water | 92.55% |
| Preservative | 0.45% |

Formulation Example 30: Conditioning Hair Rinse

| | |
|---|---|
| TEGO ®Alkanol 1618, Evonik Industries AG (INCI: Cetearyl Alcohol) | 5.0% |
| TEGO ® Alkanol CS 20 P, Evonik Industries AG (INCI: Ceteareth-20) | 0.5% |
| VARISOFT ® EQ 65, Evonik Industries AG (INCI: Distearoylethyl Dimonium Chloride; Cetearyl Alcohol) | 2.0% |
| Example 1 according to the invention | 1.3% |
| ABIL ® Quat 3474, Evonik Industries AG (INCI: Quaternium-80) | 0.5% |
| EDTA | 0.02% |
| Water | 90.68% |
| Preservative, Perfume | q.s. |

Formulation Example 31: Conditioning Hair Rinse

| | |
|---|---|
| TEGO ®Alkanol 1618, Evonik Industries AG (INCI: Cetearyl Alcohol) | 5.0% |
| TEGO ® Alkanol CS 20 P, Evonik Industries AG (INCI: Ceteareth-20) | 0.5% |
| VARISOFT ® BT 85, Evonik Industries AG (INCI: Behentrimonium Chloride) | 2.0% |
| Example 1 according to the invention | 1.3% |
| ABIL ® Quat 3474, Evonik Industries AG (INCI: Quaternium-80) | 0.5% |
| EDTA | 0.02% |
| Water | 90.68% |
| Preservative, Perfume | q.s. |

Formulation Example 32: Conditioning Hair Rinse

| | |
|---|---|
| TEGO ®Alkanol 1618, Evonik Industries AG (INCI: Cetearyl Alcohol) | 7.0% |
| TEGINACID ® C, Evonik Industries AG (INCI: Ceteareth-25) | 1.0% |
| Example 1 according to the invention | 1.0% |
| Water | 91.0% |
| Preservative, Perfume | q.s. |

Formulation Example 33: Conditioning Hair Rinse

| | |
|---|---|
| TEGO ®Alkanol 1618, Evonik Industries AG (INCI: Cetearyl Alcohol) | 7.0% |
| TEGINACID ® C, Evonik Industries AG (INCI: Ceteareth-25) | 1.0% |
| Example 1 according to the invention | 1.0% |
| ABIL ® ME 45, Evonik Industries AG (INCI: Silicone Quaternium-22; Polyglyceryl-3 Caprate; Dipropylene Glycol; Cocamidopropyl Betaine) | 1.7% |
| Water | 89.3% |
| Preservative, Perfume | q.s. |

Formulation Example 34: Conditioning Hair Rinse

| | |
|---|---|
| TEGO ®Alkanol 1618, Evonik Industries AG (INCI: Cetearyl Alcohol) | 7.0% |
| TEGINACID ® C, Evonik Industries AG (INCI: Ceteareth-25) | 1.0% |
| Example 1 according to the invention | 1.0% |
| Amodimethicone | 1.0% |
| Water | 90.0% |
| Preservative, Perfume | q.s. |

Formulation Example 35: Conditioning Hair Rinse

| | |
|---|---|
| TEGO ®Alkanol 1618, Evonik Industries AG (INCI: Cetearyl Alcohol) | 7.0% |
| TEGINACID ® C, Evonik Industries AG (INCI: Ceteareth-25) | 1.0% |
| Example 1 according to the invention | 1.0% |
| ABIL ® Soft AF 300, Evonik Industries AG (INCI: Aminopropyl Dimethicone) | 1.0% |
| Water | 90.0% |
| Preservative, Perfume | q.s. |

Formulation Example 36: Conditioning Hair Rinse

| | |
|---|---|
| TEGO ®Alkanol 16, Evonik Industries AG (INCI: Cetyl Alcohol) | 5.0% |
| TEGINACID ® C, Evonik Industries AG (INCI: Ceteareth-25) | 0.5% |
| Example 1 according to the invention | 1.0% |
| Water | 93.5% |
| Preservative, Perfume | q.s. |

Formulation Example 37: Conditioning Hair Rinse

| | |
|---|---|
| TEGO ®Alkanol 16, Evonik Industries AG (INCI: Cetyl Alcohol) | 5.0% |
| TEGINACID ® C, Evonik Industries AG (INCI: Ceteareth-25) | 0.5% |
| TEGO ®Amid S 18, Evonik Industries AG (INCI: Stearamidopropyl Dimethylamine) | 0.5% |
| Example 1 according to the invention | 0.5% |
| Water | 93.5% |
| Preservative, Perfume | q.s. |

Formulation Example 38: Conditioning Hair Rinse

| | |
|---|---|
| TEGO ®Alkanol 18, Evonik Industries AG (INCI: Stearyl Alcohol) | 5.0% |
| TEGINACID ® C, Evonik Industries AG (INCI: Ceteareth-25) | 0.5% |
| TEGO ®Amid S 18, Evonik Industries AG (INCI: Stearamidopropyl Dimethylamine) | 0.5% |
| Example 1 according to the invention | 0.5% |
| Water | 93.5% |
| Preservative, Perfume | q.s. |

Formulation Example 39: Conditioning Hair Rinse

| | |
|---|---|
| TEGO ®Alkanol 18, Evonik Industries AG (INCI: Stearyl Alcohol) | 5.0% |
| TEGINACID ® C, Evonik Industries AG (INCI: Ceteareth-25) | 0.5% |

| | |
|---|---|
| Example 1 according to the invention | 1.0% |
| Water | 93.5% |
| Preservative, Perfume | q.s. |

Formulation Example 40: Conditioning Hair Rinse

| | |
|---|---|
| TEGO ®Alkanol 1618, Evonik Industries AG (INCI: Cetearyl Alcohol) | 7.0% |
| TEGO ® Alkanol S 20 P, Evonik Industries AG (INCI: Steareth-20) | 1.0% |
| Example 1 according to the invention | 1.0% |
| Water | 91.0% |
| Preservative, Perfume | q.s. |

Formulation Example 41: Conditioning Hair Rinse

| | |
|---|---|
| TEGO ®Alkanol 1618, Evonik Industries AG (INCI: Cetearyl Alcohol) | 7.0% |
| TEGO ® Alkanol L 23 P, Evonik Industries AG (INCI: Laureth-23) | 1.0% |
| Example 1 according to the invention | 1.0% |
| Water | 91.0% |
| Preservative, Perfume | q.s. |

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein.

What is claimed is:

1. A cosmetic formulation comprising:
0.2 to 25% by weight of at least one compound of general formula I)

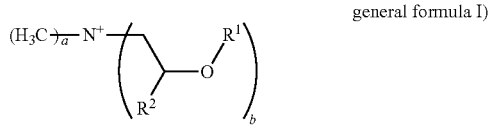

general formula I)

where $R^1$ is an acyl radical of an at least monounsaturated fatty acid with a chain length of 18 to 24 carbon atoms or an acyl radical of isostearic acid or ricinoleic acid,
$R^2$ is an alkyl radical having 1 to 6 carbon atoms,
a=1 to 3, and
b=1 to 3, with the proviso that a+b=4,
2.0 to 7.0% by weight of a mixture of fatty alcohols having 16 and 18 carbon atoms,
0.1 to 7% by weight of at least one compound of general formula II

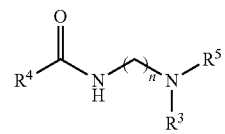

II where $R^4$—CO is selected from aliphatic, linear or branched acyl radical having 6 to 22 carbon atoms and 0, 1, 2 or 3 double bonds,
$R^3$ and $R^5$ are selected from identical or different alkyl radicals, which can optionally be substituted with polar groups,
n is an integer selected from 1 to 10; and the formulation further comprises
40 to 99.8% by weight of water,
where the percentages by weight refer to the total formulation.

2. The cosmetic formulation according to claim 1, further comprising up to 8% by weight of a compound of general formula Ia)

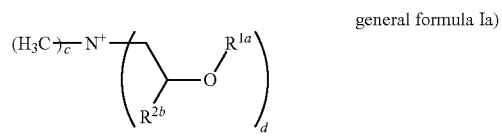

general formula Ia)

where $R^{1a}$ is an acyl radical of another carboxylic acid as defined for $R^1$ and
$R^{2b}$ is an alkyl radical having 1 to 6 carbon atoms,
c=1 to 3, and
d=1 to 3, with the proviso that c+d=4,
where the percentages by weight refer to the total formulation, and wherein the at least one compound of general formula I) constitutes at least 30% by weight, based on all of the compounds of general formula I) and Ia) present in the formulation.

3. The cosmetic formulation according to claim 1, wherein $R^1$ is selected from the acyl radicals of the acids selected from the group consisting of oleic acid, elaidic acid, vaccenic acid, gadoleic acid, icosenoic acid, cetoleic acid, erucic acid, nervonic acid, linoleic acid, alpha-linolenic acid, gamma-linolenic acid, calendula acid, punicic acid, alpha-elaeostearic acid, beta-elaeostearic acid, arachidonic acid, timnodonic acid, clupanodonic acid, and cervonic acid.

4. The cosmetic formulation according to claim 1, wherein
a=b=2.

5. The cosmetic formulation according to claim 1, wherein said formulation contains no fatty acids or fatty acid salts.

6. The cosmetic formulation according to claim 1, wherein the fatty alcohol is selected from the group consisting of octanol, decanol, lauryl alcohol, isolauryl alcohol, anteisolauryl alcohol, myristyl alcohol, isomyristyl alcohol, cetyl alcohol, palmoleyl alcohol, stearyl alcohol, isostearyl alcohol, anteisostearyl alcohol, eicosanol, petroselinyl alcohol, Guerbet alcohol, arachyl alcohol, gadoleyl alcohol, behenyl alcohol, erucyl alcohol, hectacosanol, octacosanol, melissyl alcohol, and mixtures thereof.

7. The cosmetic formulation according to claim 1, further comprising at least one counterion to the compound of general formula I), wherein said at least one counteranion is selected from the group consisting of chloride, bromide, iodide, alkyl sulphate, alkylsulphonate, triflate, tosylate, phosphate, sulphate, hydrogensulphate, lactate, glycolate, acetate and citrate.

8. The cosmetic formulation according to claim 1, wherein the compound of general formula I and compound of general formula II are present, respectively, in a weight ratio of 20:1 to 1:20.

9. The cosmetic formulation according to claim 1, wherein the compound of general formula I and compound of general formula II are present, respectively, in a weight ratio of 10:1 to 1:10.

10. The cosmetic formulation according to claim 1, wherein the compound of general formula I and compound of general formula II are present, respectively, in a weight ratio of 5:1 to 1:5.

11. The cosmetic formulation according to claim 1, wherein the compound of general formula I and compound of general formula II are present, respectively, in a weight ratio of 3:1 to 1:3.

12. The cosmetic formulation according to claim 1, wherein the mixture of fatty alcohols having 16 and 18 carbon atoms is a mixture of coconut or tallow fatty alcohols.

13. A method of treating keratin fibers, said method comprising applying a cosmetic formulation according to claim 1 to keratin fibers.

\* \* \* \* \*